Figure 1:
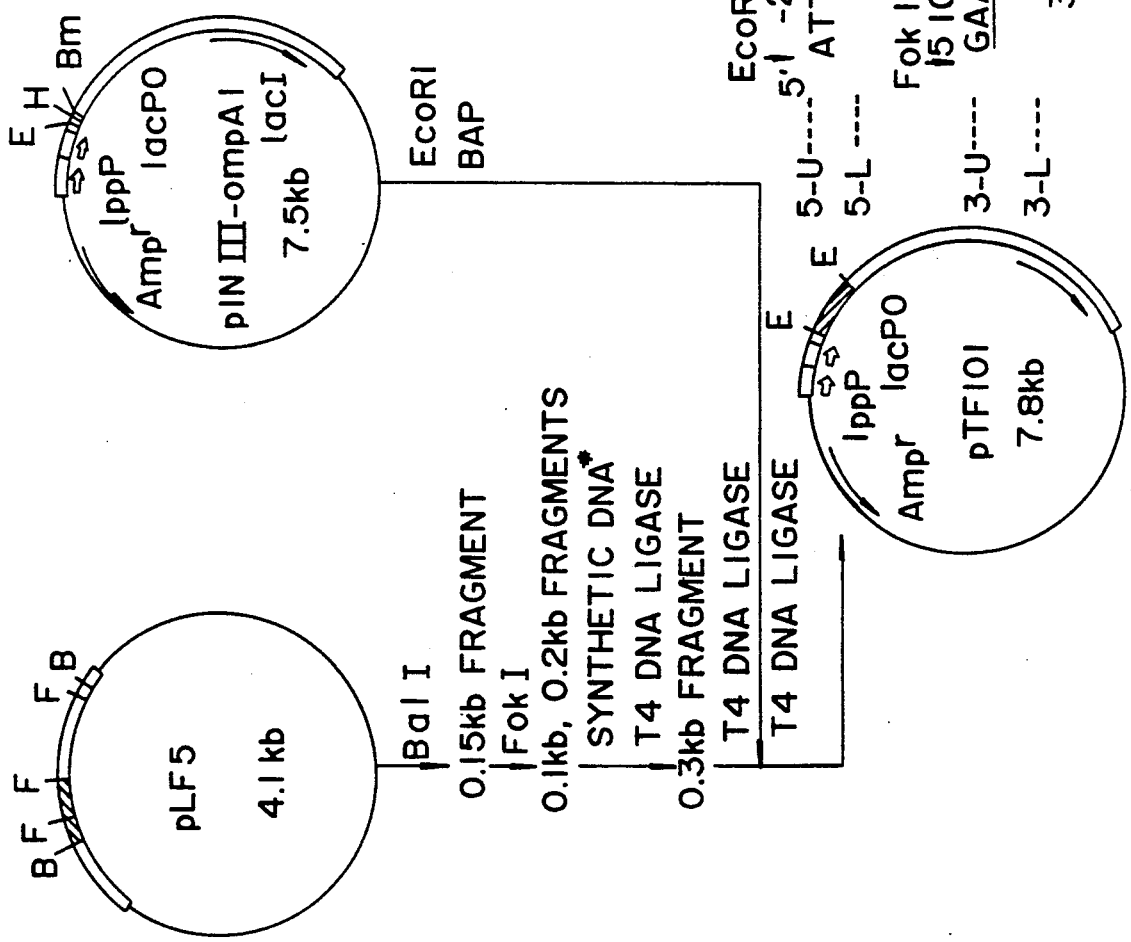

United States Patent [19]

Kimizuka et al.

[11] Patent Number: 5,102,988

[45] Date of Patent: * Apr. 7, 1992

[54] POLYPEPTIDE WITH CELL-SPREADING ACTIVITY

[75] Inventors: Fusao Kimizuka, Ohmihachiman; Shouichi Goto, Otsu; Yoh'ichi Ohdate, Amagasami; Masamitsu Shimada, Otsu; Ikunoshin Kato, Uji, all of Japan

[73] Assignee: Takara Shuzo Co., Ltd., Kyoto, Japan

[ * ] Notice: The portion of the term of this patent subsequent to Sep. 3, 2008 has been disclaimed.

[21] Appl. No.: 362,983

[22] Filed: Jun. 8, 1989

[30] Foreign Application Priority Data

Jun. 30, 1988 [JP] Japan ................................ 63-160949

[51] Int. Cl.$^5$ ............................................. C07K 13/00
[52] U.S. Cl. ..................................... 530/350; 530/382
[58] Field of Search ................................ 530/350, 382

[56] References Cited

U.S. PATENT DOCUMENTS

| 4,517,686 | 5/1985 | Ruoslahti et al. | 530/350 |
| 4,589,881 | 5/1986 | Pierschbacher et al. | 530/350 |
| 4,614,517 | 9/1986 | Ruoslahti et al. | 530/330 |

FOREIGN PATENT DOCUMENTS 0207751 6/1986 European Pat. Off. .

OTHER PUBLICATIONS

The Journal of Biological Chemistry, "The Interaction of Fibronectin Fragments with Fibroblastic Cells", vol. 260, No. 24, Issue of Oct. 25, pp. 13256–13260, 1985.
The Journal of Biological Chemistry, "Domain Structure of the Carboxylterminal Half of Human Plasma", vol. 258, No. 5, Issue of Mar. 10, pp. 3332–3340, 1983.
K. Sekiguchi and S. Hakomori, "Functional Domain Structure of fibronectin." Proc. Natl. Acad. Sci, U.S.A., 77, 2661–2665, May 1980.
M. D. Pierschbacher, E. G. Hayman and E. Ruoslahti, "Location of the Cell-Attachment Site in Fibronectin with Monoclonal Antibodies and Proteolytic Fragments of the Molecule." Cell, 26, 259–267, Oct. 1981.
M. D. Pierschbacher and E. Ruoslahti, "The Cell Attachment Domain of Fibronectin. Determination of the Primary Structure." J. Biol. Chem., 257, 9593–9597, Aug. 1982.
M. D. Pierschbacher, E. G. Hayman and E. Ruoslahti, "Synthetic Peptide with Cell Attachment Activity of Fibronectin." Proc. Natl. Acad. Sci. U.S.A., 80, 1224–1227, Mar. 1983.
M. D. Pierschbacher and E. Ruoslahti, "Cell Attachment Activity of Fibronectin Can Be Duplicated by Small Synthetic Fragments of the Molecule." Nature, 309, 30–33, May 1984.
A. R. Kiornblihtt, K. Vibe-Pedersen and F. E. Baralle, "Human Fibronectin: Cell Specific Alternative mRNA Splicing Generates Polypeptide Chains Differing in the Number of Internal Repeats." Nucl. Acids. Res., 12, 5853–5868, Jul. 1984.
M. D. Pierschbacher and E. Ruoslahti, "Variants of the Cell Recognition Site of Fibronectin that Retain Attachment-Promoting Activity." Proc. Natl. Acad. Sci. U.S.A., 81, 5985–5988, Oct. 1984.
A. R. Kornblihtt, K. Umezawa, K. Vibe-Pedersen and F. D. Baralle, "Primary Structure of Human Fibronectin: Differential Splicing May Generate at Least 10 Polypeptides From a Single Gene." EMBO J., 4, 1755–1759, 1985.
S. K. Akiyama, E. Hasegawa, T. Hasegawa and K. M. Yamada, "The Interaction of Fibronectin Fragments with Fibroblastic Cells." J. Biol. Chem., 260, 13256–13260, Oct. 1985.
M. Obara, M. S. Kang, S. Rocher-Dufour, A. Kornblihtt, J. P. Thiery and K. M. Yamada, "Expression of the Cell-Binding Domain of Human Fibronectin in *E. coli.*" FEBS Lett., 213, 261–264, Mar. 1987.

*Primary Examiner*—Margaret Moskowitz
*Assistant Examiner*—Shelly J. Guest
*Attorney, Agent, or Firm*—Armstrong, Nikaido, Marmelstein, Kubovcik & Murray

[57] ABSTRACT

A polypeptide having the cell-spreading activity of human fibronectin. Methods of preparing the polypeptide are described.

1 Claim, 4 Drawing Sheets

POLYPEPTIDE WITH CELL-SPREADING ACTIVITY

This invention relates to a protein which has cell-spreading activity like that of fibronectin. More particularly, the invention relates to a polypeptide which has the cell-spreading activity of fibronectin of human origin; and also to a method for the preparation of said polypeptide.

Fibronectin is a multifunctional glycoprotein which is widely distributed in a variety of animal tissues and body fluids and also on the surface of cultured cells and elsewhere. This compound has various physiological effects, such as causing attachment, spreading, migration, differentiation, proliferation, and phagocytosis by cells, among others. This glycoprotein participates in such activities as tissue reconstruction, tissue construction, and protection from infection.

Fibronectin is a polypeptide with a molecular weight of about 250,000 and is a dimer with an S-S bond in the vicinity of the C-terminus. The amino acid sequence of this molecule contains 3 different types of internal repeats, and can be classified as types I, II and III. In addition, there are domain structures which have various functions, with the effect of cell attachment and spreading and the ability to bind to collagen, heparin, fibrin, etc. Of these domains, industrial applications of the biological activity related to the cell attachment and spreading domain have been considered; for example, in the preparation of a coating agent for a substrate for culture, it is possible to use this function in the preparation of a substrate to which cells will bind. Also, this function can be used as an accelerator of cell binding in such preparations as collyrium, lotions, and agents for the healing of wounds. Cell spreading is a phenomenon that follows after cell attachment. For cells to proliferate, with some exceptions, it is necessary for the phenomenon of spreading to take place, not cell attachment alone.

The basic structure which is the minimum essential structure for the cell-attachment domain of fibronectin is the sequence Arg-Gly-Asp-Ser (*Nature*, 309 1984, 30–33). Japanese Laid-Open Patent (Tokuhyo) 84-501548 discloses a peptide with cell-attachment activity, that is a polypeptide of the molecular weight of 11,500 and that contains this sequence among its sequence with 108 amino acid residues.

However, the cell-attachment activity of this polypeptide with the molecular weight of 11,500 is much weaker than that of fibronectin of natural origin, and it is not necessarily possible to make use of it in the practical applications mentioned above. This difficulty is discussed, for example, in *J. Biol. Chem.*, 260 (1985), 13256-13260. Also, the inventors of this invention have constructed the polypeptide of the molecular weight of 11,500 mentioned above by means of genetic engineering, and compared its cell-spreading activity to that of fibronectin of natural origin with the use of normal rat kidney (NRK) cells. The results were that, whereas fibronectin gave noticeable activity at the dose of 0.1-1 μg/well, the dose of 50 μg/well of the polypeptide with the molecular weight of 11,500 did not have any such activity.

The object of this invention is to identify the amino acid sequence that has substantial cell-spreading activity as the peptide of the cell-spreading domain of fibronectin and to provide a method for producing the same.

Briefly the present invention relates to polypeptides with cell-spreading activity, which have an amino acid sequence represented by the following general formula [I]:

| | | | | Pro | Thr | Asp | Leu | Arg | Phe | Thr | Asn | Ile | Gly | Pro | Asp | [I] |
|---|---|---|---|---|---|---|---|---|---|---|---|---|---|---|---|---|
| Thr | Met | Arg | Val | Thr | Trp | Ala | Pro | Pro | Pro | Ser | Ile | Asp | Leu | Thr | Asn | |
| Phe | Leu | Val | Arg | Tyr | Ser | Pro | Val | Lys | Asn | Glu | Glu | Asp | Val | Ala | Glu | |
| Leu | Ser | Ile | Ser | Pro | Ser | Asp | Asn | Ala | Val | Val | Leu | Thr | Asn | Leu | Leu | |
| Pro | Gly | Thr | Glu | Tyr | Val | Val | Ser | Val | Ser | Ser | Val | Tyr | Glu | Gln | His | |
| Glu | Ser | Thr | Pro | Leu | Arg | Gly | Arg | Gln | Lys | Thr | Gly | Leu | Asp | Ser | Pro | |
| Thr | Gly | Ile | Asp | Phe | Ser | Asp | Ile | Thr | Ala | Asn | Ser | Phe | Thr | Val | His | |
| Trp | Ile | Ala | Pro | Arg | Ala | Thr | Ile | Thr | Gly | Tyr | Arg | Ile | Arg | His | His | |
| Pro | Glu | His | Phe | Ser | Gly | Arg | Pro | Arg | Glu | Asp | Arg | Val | Pro | His | Ser | |
| Arg | Asn | Ser | Ile | Thr | Leu | Thr | Asn | Leu | Thr | Pro | Gly | Thr | Glu | Tyr | Val | |
| Val | Ser | Ile | Val | Ala | Leu | Asn | Gly | Arg | Glu | Glu | Ser | Pro | Leu | Leu | Ile | |
| Gly | Gln | Gln | Ser | Thr | Val | Ser | Asp | Val | Pro | Arg | Asp | Leu | Glu | Val | Val | |
| Ala | Ala | Thr | Pro | Thr | Ser | Leu | Leu | Ile | Ser | Trp | Asp | Ala | Pro | Ala | Val | |
| Thr | Val | Arg | Tyr | Tyr | Arg | Ile | Thr | Tyr | Gly | Glu | Thr | Gly | Gly | Asn | Ser | |
| Pro | Val | Gln | Glu | Phe | Thr | Val | Pro | Gly | Ser | Lys | Ser | Thr | Ala | Thr | Ile | |
| Ser | Gly | Leu | Lys | Pro | Gly | Val | Asp | Tyr | Thr | Ile | Thr | Val | Tyr | Ala | Val | |
| Thr | Gly | Arg | Gly | Asp | Ser | Pro | Ala | Ser | Ser | Lys | Pro | Ile | Ser | Ile | Asn | |
| Tyr | Arg | Thr | Glu | Ile | Asp | | | | | | | | | | | |

This invention also relates to recombinant plasmids which contain the DNA which codes for the polypeptides with cell-spreading activity having the structure represented by the above general formula [I], and this invention also relates to transformants which carry these recombinant plasmids. The present invention further relates to a method for the preparation of the polypeptides having the structure of the general formula [I] with cell-spreading activity by the cultivation of these transformants and the collection of the polypeptides from the culture medium.

We have found that the polypeptide for which the above mentioned patent application has been filed as having cell attachment activity and which is a polypeptide of 11.5-kDa (with a sequence of 108 amino acids) of fibronectin nectin of human origin (abbreviated FN below), has almost no cell-spreading activity, but that the peptide with the sequence of 283 amino acids (Ala[1235]-Met[1517]) that extends from the N-terminus of said polypeptide does have about the same level of spreading activity as FN; and have accomplished a method for its preparation by use of the techniques of genetic engineering, for which a Japanese patent application was filed on Jan.5, 1988, with the title of the invention "Polypeptide with cell-spreading activity" (Japanese Patent Application No. 148/88, U.S. patent application Ser. No. 07/291,894 (Dec. 29, 1988)).

In this specification, the superscript numerals affixed to the symbols for amino acids show the number of the amino acid residue counted from the N-terminus of the amino acids of FN based on the EMBL Data Bank.

We have further proceeded research work and have prepared by the use of the techniques of genetic engineering polypeptides with cell-spreading activity which have different chain lengths because of the deletion of amino acid or peptide from the N-terminus of the peptide having a sequence of 283 amino acid residues. We have measured the cell-spreading activity of these polypeptides, and have made clear the relationship between the chain length of the peptide and the cell-spreading activity. Further, in the course of such research work it has been found that there occurs a remarkable change in the expression of the peptide depending on the amino acid sequence in the region of the N-terminus. As a result thereof it has become possible to identify the sequence of a peptide which can be expressed in large amounts in addition to its high level of cell-spreading activity, for which a Japanese patent application was filed on Feb. 16, 1988, with the title of invention "Polypeptide with cell-spreading activity" (Japanese Patent Application No. 31820/88, U.S. patent application No. 07/310,170 (Feb. 13, 1989), European Patent Aplication No. 89301440.7 (Feb. 15, 1989)) including a peptide with a sequence of 279 amino acids($Pro^{1239}$-$Met^{1517}$).

Through continued research, we have prepared a peptide with a sequence of 274 amino acids($Pro^{1239}$-$Asp^{1512}$) by the deletion by genetic engineering techniques of five amino acid residues from the C-terminal side of the peptide with a sequence of 279 amino acids(-$Pro^{1239}$-$Met^{1517}$) and found by mesurement of its cell-spreading activity that it has about the same level of spreading activity as FN. This invention is based upon those findings.

The invention will be explained in more detail below.

The preparation by genetic engineering techniques of a plasmid that codes for the peptide with a sequence of 279 amino acids($Pro^{1239}$-$Met^{1517}$) is by the methods that has been disclosed in Japanese Patent Application No. 148/88 and 31820/88.

The complete amino acid sequence of fibronectin of human origin and its cDNA sequence were published in The *EMBO Journal*, 4 (1985), 1755-1759. The steps by which the cDNA corresponding to the amino acid sequence of the cell attachment and spreading domain of fibronectin can be cloned are well known. For example, an RNA fraction containing poly(A) from the liver is prepared, and a cDNA library can be prepared by such method as the Okayama-Berg method or the Gubler-Hoffmann method. Alternatively, such cDNA libraries are commercially available. Thus it is possible to obtain them from, for example, the Clontech Laboratories, Inc. As a method to obtain the desired cDNA clone from the cDNA library, the DNA which corresponds to the amino acid sequence can be used as a probe with the techniques of colony hybridization or plaque hybridization. The clones which hybrized with the probe are selected, and DNA is extracted from the cell pellet or a phage lytic solution and cleaved with restriction enzymes. Insertions are confirmed by the use of electrophoresis. When necessary, Southern blotting is used to check the insert being hybridized with the probe. In the final step, by the study of the base sequence of the insert by the dideoxy method or the like, the identity of the desired clone can be checked.

When necessary, the vector which carried the cDNA coding for the cell-spreading domain of fibronectin can be amplified in the host cells, purified, and cleaved with restriction enzymes so that the cDNA portion can be removed; electrophoresis can be used to purify the cDNA fragments. These cDNA fragments are joined by use of a DNA ligase by inframe ligation to expression vectors, and by their introduction to host cells, it is possible to express the cDNA. Any of the known vectors can be used as expression vectors for *Escherichia coli* as the host, but for preference, a host-vector system which can have its expression induced and which has strong promoter activity is used. As such vectors, there are, for example, the vector which carries the λPL promoter, the vector which carried the lac promoter, the vector which carries the trp promoter, the vector which carries the pst promoter, the vector which carries both the lac and the trp promoters, the vector which carries the lpp promoter, the vector which carries both the lpp and lac promoters, and other such known vectors (refer to Yoshiyuki Sakai, "Vector DNA", Kodansha Scientific, 1986).

Also, it is possible to use vectors in which exogenous genes can be inserted downstream from a gene for a signal peptide so that the peptide which has been expressed can be secreted.

When a peptide is expressed by the gene for the desired peptide by the use of an expression vector which can be joined downstream from a gene for a signal peptide or by the use of an expression vector directly, by the joining of the vector, sometimes a certain length of the amino acid sequence of vector origin are connected to the N-terminus of the desired peptide. By the addition of this sequence, there is caused no essential change in the cell-spreading activity of the polypeptide, and it is possible to use the polypeptide as is. However, it is possible, whenever necessary, to remove this sequence by the techniques of gene engineering. This removal involves what is called site-specific mutagenesis, which is a well-established technique.

Thus, first, an appropriate restriction enzyme is used to cleave one site slightly upstream of the initiation codon of pTF301 that codes for the sequence $Ala^{1235}$-$Met^{1517}$ of FN, and then exonuclease is used, by which means it is possible to remove the 5'-end of the sequence. By changes in the reaction conditions, it is possible to obtain a plasmid from which appropriate portions of the 5'-terminus of the coding region have been deleted. Then an appropriate restriction enzyme is used to cleave a site slightly downstream from the termination codon of the coding region of these plasmids, and the DNA which has been cleaved is separated by gel electrophoresis, by which it is possible to obtain fragments of cDNA from which various portions of the 5'-terminal strand have been removed. By the insertion of these cDNA fragments into an appropriate expression vector, it is possible to express peptides of various lengths wherein portions of the N-terminal region of the sequence of $Ala^{1235}$-$Met^{1517}$ (283 amino acid residues) have been deleted.

As the expression vector, any of the well-known vectors can be used. We have obtained satisfactory results with direct expression by the use of the pUC-type vectors in which the distance between the ribosome-binding site and the initiation codon has been made optimum.

Also, by the joining with a transcription-termination signal downstream from the termination (stop) codon of pUC vectors, it is possible to improve the expression level.

Selection of the recombinants which express the peptide with cell-spreading activity can be done conveniently with immunoscreening. That is, expression vectors to which the cDNA fragments of different lengths have been joined are inserted into cells of *Escherichia coli* by the usual methods, and the transformants obtained are raised on nitrocellulose filters, after which they are lysed, and the protein from the cells is fixed on the filters. After the filters are blocked with bovine serum albumin or the like, a monoclonal antibody which recognizes the domain of cell spreading of FN is caused to act. The monoclonal antibody bound to the filter is detected by labelling with a second antibody. In this way, it is possible to select recombinants that express the peptide with the domain for cell spreading.

Next, the recombinants so selected are cultured under conditions suitable for expression, and expression of the peptide with the domain for cell spreading is induced. For verification that expression is taking place, immuno-blotting can be used. Thus, the whole-cell protein of the cultured cells is lysed by heat treatment in a buffer containing SDS, and separation is conducted on SDS-polyacrylamide electrophoresis, and the electrophoretic pattern is transferred to a nitrocellulose or nylon membrane. After a monoclonal antibody specific for the cell-spreading domain of FN is incubated with the membrane, an enzyme-labeled second antibody is applied, and the enzyme activity of the bound antibody gives rise to color in a chromogenic material, thereby it is possible to confirm that there is a band of the peptide with the cell-spreading domain.

Also by analysis of the base sequence of the 5'-end of the insert fragments of the clones that are obtained, it is possible to identify the N-terminus of the peptide that is expressed.

For the method for the preparation by means of genetic engineering of the peptide with the sequence of 274 amino acids($Pro^{1239}$-$Asp^{1512}$), it is convenient to use the plasmid pTFD707 that code for the sequence of 279 amino acids($Pro^{1239}$-$Met^{1517}$). By the replacement of the codon, AAA, for the fifth amino acid, $Lys^{1513}$, from the C-terminus of the peptide with a sequence of 279 amino acids with the termination codon TAA, it is possible to prepare a plasmid that codes for the peptide with a sequence of 274 amino acids($Pro^{1239}$-$Asp^{1512}$). The replacement of this base can be done by means of site specific mutagenesis.

Purification of the peptide with the domain for cell spreading from the recombinants can be done, for example, as follows. The cell pellet is suspended in a buffer, and the soluble fraction and insoluble fraction are separated by ultrasonification. The insoluble fraction is solubilized in a buffer which contains 7 M urea. The soluble fractions are pooled, and put on a Sepharose 4B column bound with the antibody used in immunoblotting; then, affinity purification is carried out. For elution there is used a buffer in the pH region of 2.3. By the collection of the desired fractions by immunoblotting, it is possible to collect the peptide with the domain for cell spreading. When necessary, further purification by FPLC and HPLC can be done.

The peptide with the cell-spreading domain thus obtained may be measured for its cell-spreading activity toward NRK (normal rat kidney) cells. The sample is dissolved in a buffer, and used to coat microtiter plate wells, after which NRK cells are added, and the plate is incubated for a fixed time at 37° C. The spreading of the cells is observed under a microscope, and the minimum dose of sample per well that gives rise to the expression of cell-spreading activity is compared to the dose needed of FN of natural origin. In this way, the strength of the cell-spreading activity can be expressed.

By the series of experiments described above, it has been found that the peptide with the sequence of 274 amino acids($Pro^{1239}$-$Asp^{1512}$) that has the sequence shown in general formula I shown above has essentially the same cell-spreading activity as that of FN.

Figure 2:
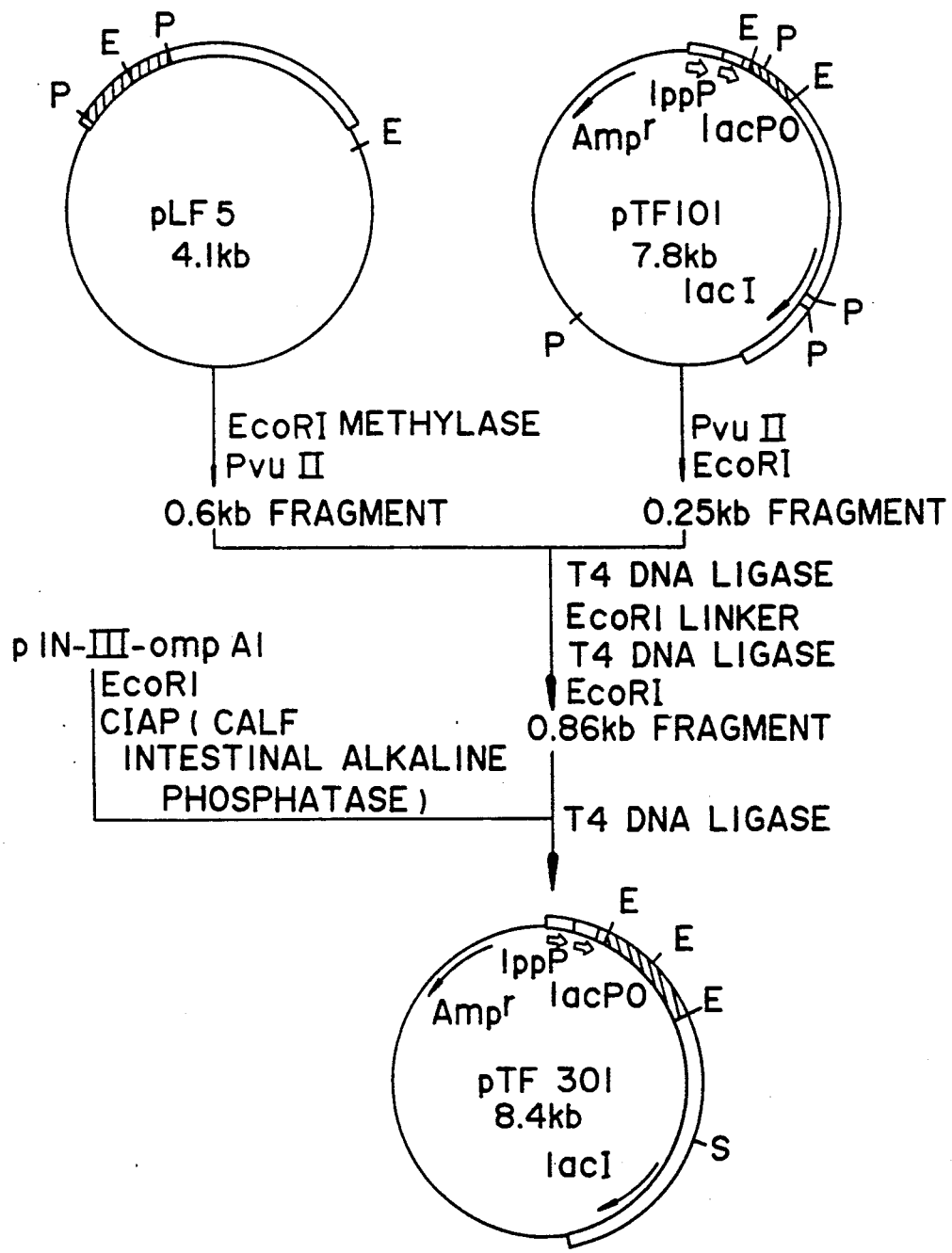
Figure 3:
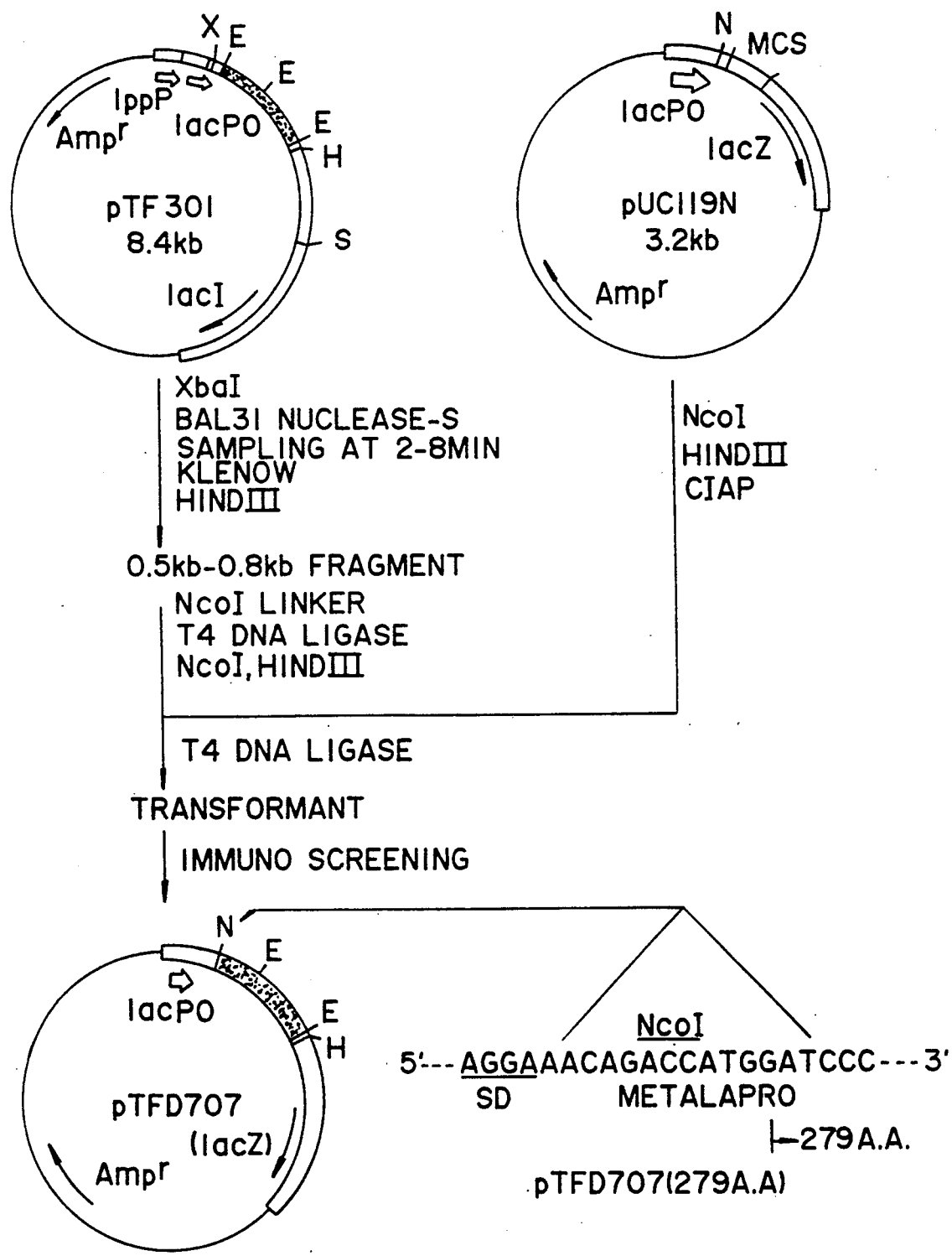
Figure 4:
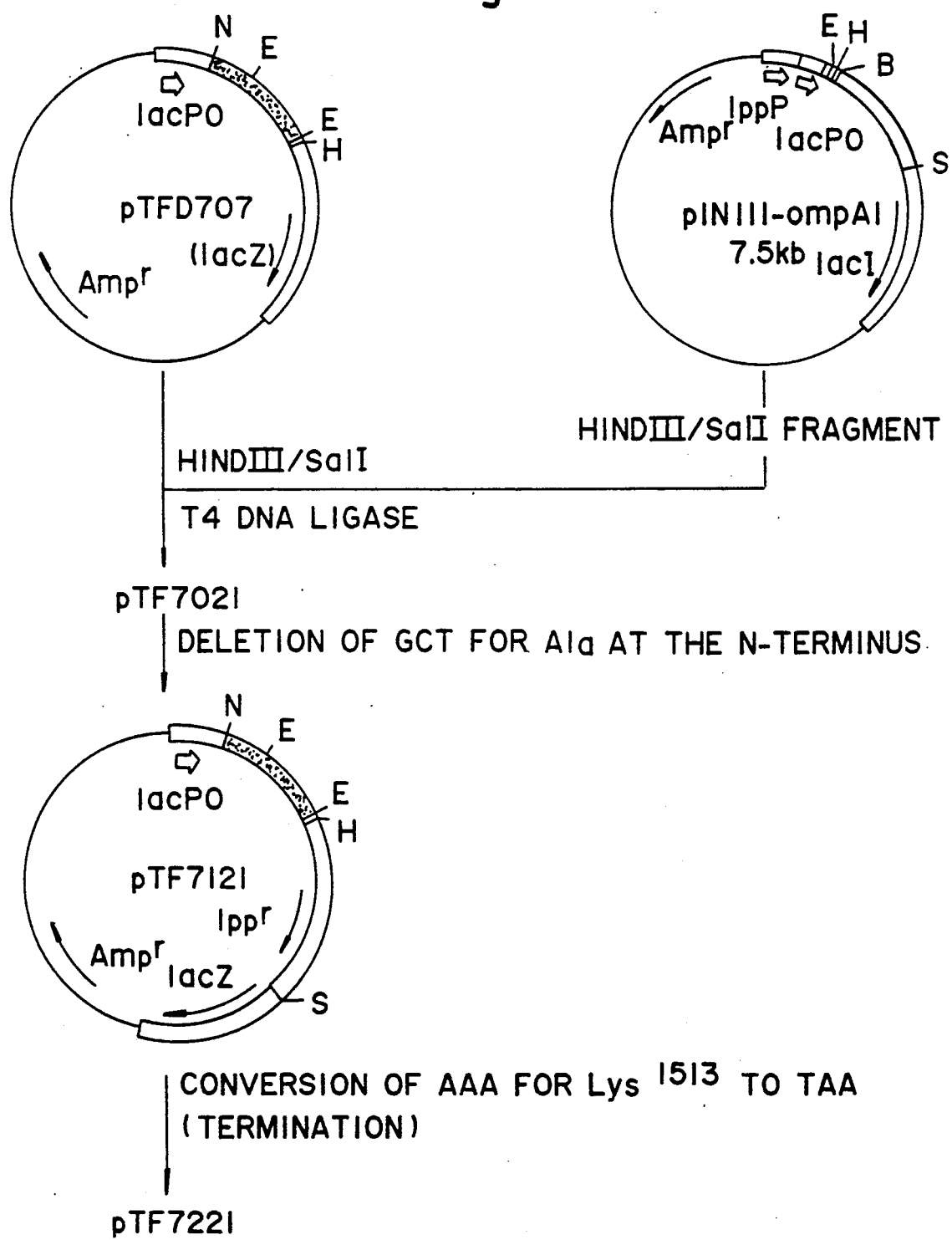

The invention will be further explained in more detail by the following Examples, which partly refer to the accompanying drawings wherein;

FIG. 1 is a diagram of the processes involved in the construction of an expression plasmid which carries the DNA sequence which codes for the polypeptide including the $Ile^{1410}$-$Met^{1517}$ sequence of fibronectin, FIG. 2 is a diagram of the processes involved in the construction of an expression plasmid which carries the DNA sequence which codes for the polypeptide including the $Ala^{1235}$-$Met^{1517}$ sequence of fibronectin, FIG. 3 is a diagram of the processes involved in the construction of an expression plasmid which carries the DNA sequence which codes for the polypeptide including the $Pro^{1239}$-$Met^{1517}$ sequence of fibronectin, and FIG. 4 is a diagram of the process involved in the construction of an expression plasmid which carries the DNA sequence which codes for a polypeptide including the $Pro^{1239}$-$Asp^{1512}$ sequence of fibronectin.

EXAMPLE 1

Cloning of the cDNA fragment which codes for $Ile^{1410}$-$Met^{1517}$ (108 amino acid residues) of fibronectin (see FIG. 1):

(1-1) Preparation of cDNA fragments

First, 100 μg of a plasmid, pLF5 (reported in *Biochemistry*, 25 [1986], 4936–4941) which is of 4.1 kilobases and which contains the cDNA sequence which codes for the cell-spreading domain of fibronectin was put into 200 μl of a reaction mixture containing a buffer for use with the restriction enzyme BalI and 100 units of BalI, and the mixture was incubated for 2 hours at 37° C. The reaction mixture was then put on an HPLC column of DEAE-4000 (6×125 mm; Nucleogen) and eluted with a concentration gradient of KCl in a 30 mM potassium phosphate buffer (pH 6.5) which contains 5M urea, and precipitated with isopropyl alcohol, which gave 7.5 μg of 0.75 kb fragments. Next, these fragments were treated with 30 units of FokI for 1 hour at 37° C., and by the same purification method, 60 ng of 92-bp fragments and 140 ng of 203-bp fragments were obtained.

(1-2) Preparation of synthetic DNA linker

So that the cDNA fragments could be joined to a vector, 5'-end and 3'-end linkers were chemically synthesized by the following method. The base sequence is shown in FIG. 1. The upper strand of the 5'-end linker (chain length, 11), labelled 5 U, the lower strand of the 5'-end linker (chain length, 7), labelled 5 L, the upper strand of the 3'-end linker (chain length, 30), labelled 3 U, and the lower strand of the 3'-end linker (chain length, 30), labelled 3 L, were synthesized by use of the DNA synthesizer of Applied Biosystems, Inc. After deprotection, 5 U and 5 L were purified by ion-exchange HPLC on a TSK gel DEAE-2000 column, and desalted on SepPak (Waters), giving 60 μg and 40 μg, respectively. 3 U and 3 L were separated by 12% polyacrylamide gel electrophoresis which contains 7M urea, and after they were removed from the gel, they were desalted in the same way as for the 5 U and 5 L, giving 32 μg and 26 μg, respectively. The base sequences were checked by the solid-phase MaxamGilbert method. Each strand was then phosphorylated on its 5' terminus in the following way. First, 25 μg of DNA was dissolved in 10 μl of distilled water, and put into 20 μl of a solution of buffer for use with polynucleotide Kinase (PNK) containing 50 mM Tris-HCl, pH 7.6, 10 mM $MgCl_2$, and 10 mM DTT, 1 mM ATP, and 5 units of PNK; the mixture was incubated for 1 hour at 37° C.; then the reaction was stopped by heat treatment at 65° C. for 10 minutes. After the phosphorylation, by the annealing of 5 U with 5 L and of 3 U with 3 L, the strands were made double-stranded. That is, equal amounts of 5 U and 5 L were mixed together, and left at 60° C. for 10 minutes, after which the mixture was allowed to cool to room temperature gradually, and then cooled further to 15° C. The 3 U and 3 L were treated in the same way.

(1-3) Binding of cDNA fragments and the linkers

The two kinds of linkers prepared in section (1-2) above and the two kinds of DNA fragments (with 92 bp and with 203 bp) prepared in section (1-1) above were used, and ligated together. For this, 0.5 pmol of each kind of cDNA fragment and 5 pmol of each kind of linker were put into 20 μl of a solution containing a ligation buffer [66 mM Tris-HCl, pH 7.6, and 6.6 mM $MgCl_2$] and also 0.5 mM ATP, 10 mM DTT, and 2.8 units of T4 DNA ligase, at 16° C.; the mixture was incubated overnight. The reaction mixture was heated for 10 minutes at 65° C., and then two volumes of cold ethanol was added, and the whole left at −70° C. for 30 minutes. After this, the precipitated DNA was collected by centrifugation. This DNA was put into 20 μl of a reaction mixture made of buffer for use with EcoRI and 7.5 units of EcoRI, and incubated for 30 minutes at 37° C. Then the mixture was subjected to polyacrylamide electrophoresis, thereby 336-bp fragments were obtained. These were extracted for 10 hours at 37° C. in a gel elution buffer (0.5M ammonium acetate, 0.01M magnesium acetate, and 1 mM EDTA), after which the fragments were precipitated with ethanol, and the DNA was collected. This DNA was dissolved in 20 μl of TE buffer (10 mM Tris-HCl and 1 mM EDTA, pH 8.0).

(1-4) Binding of cDNA fragments bound with linkers to a vector

First, 1 ug of the secretion-expression vector pIN-III-ompA-1 (reported in the *EMBO Journal*, 3 [1984], 2437–2442) was incubated together with 5 units of EcoRI in buffer for use with EcoRI for 1 hour at 37° C., and next, 0.5 unit of alkaline phosphatase was added; and incubation continued for another hour. The reaction mixture was treated twice with phenol, and ethanol precipitation was used to give 0.5 μg of DNA. This DNA was cleaved with EcoRI, and then 0.1 μg of dephosphorylated pIN-III-ompA-1 vector was put into a mixture with 0.1 μg of the DNA fragments obtained in section (1-3) above together with 10 μl of buffer for use with T4 DNA ligase, 0.5 mM ATP, 10 mM DTT, and 1.8 units of T4 DNA ligase, in a total volume for the reaction mixture of 30 μl. This mixture was incubated overnight at 16° C. Then 15 μl of this reaction mixture was used in the transformation of *Escherichia coli* cells.

(1-5) Transformation of cells of *Escherichia coli*

Cells of *Escherichia coli* SB221 (The *EMBO Journal*, 3 [1984], 2437–2442) were put into a 20 ml test tube containing 5 ml of L-broth (Bactotrypton, 10 g/l; yeast extract, 5 g/l; NaCl, 5 g/l; pH 7.2) and cultured overnight with agitation at 37° C. Then 0.05 ml of this culture broth was used to inoculate 5 ml of fresh L-broth, and culture was continued with agitation until the absorbance at 600 nm reached 0.6. This culture broth was cooled over ice and centrifuged for 5 minutes at 5000 rpm at 4° C. The supernatant was removed. This was mixed with 2.5 ml of an ice-cold 0.1M $MgCl_2$ solution, after which it was centrifuged in the same way and the supernatant removed. This was mixed with 1.25 ml of ice-cold 0.1M $CaCl_2$, immediately mixed with ice-water, and left for 30 minutes. The mixture was centrifuged and the supernatant removed; then it was mixed with 0.1 ml of ice-cold 0.1M $CaCl_2$ to suspend it rapidly. The suspension was mixed with 10 μl of the reaction mixture obtained in section (1-4) above, and left for 30 minutes in an ice bath. Next, it was heated to 42° C. for 2 minutes. Then, 1 ml of L-broth heated to 37° C. was added, and the whole was incubated for 30 minutes at 37° C. After this, the mixture was cultured for 1 hour at 37° C. with agitation. The culture broth was spread on L agar medium that contained 50 μg/ml ampicillin, and colonies which grew after overnight culture at 37° C. were isolated. About 200 colonies were obtained, and fourteen of these were analyzed for plasmids.

(1-6) Analysis of Plasmids

After 14 transformants were cultured with agitation overnight in 1.5 ml of L-broth containing 50 μg/ml ampicillin, the cultures were centrifuged and the cell pellets were obtained. The cell pellets were suspended in 100 μl of solution A (50 mM glucose, 10 mM EDTA, 25 mM Tris-HCl, pH 8.0, and 2 mg/ml lysozyme), and left at room temperature for 5 minutes. Then 200 μl of solution B (0.2N NaOH and 1% SDS) was added to the suspension, and the container was rapidly inverted five times and then left at 0° C. for 10 minutes. To the container, 150 μl of 5M potassium acetate (pH 5.0) was added, followed by the addition of two volumes of cold ethanol, and the mixture was left at −70° C. for 30 minutes, after which it was centrifuged and the DNA was obtained. The DNA was washed with 80% ethanol, and the ethanol and water were removed under reduced pressure. The residue was dissolved in a small amount of TE buffer. One portion of the solution (0.1 μg) was allowed to react for 1 hour at 37° C. in 10 μl of a reaction mixture which contains 5 units of EcoRI in buffer for use with EcoRI. Then the reaction mixture was separated on agarose electrophoresis, and the expected bands for DNA (at 0.33 kb) were checked by ethidium bromide staining. The results showed that nine of the clones gave the desired band. The plasmids extracted from these nine clones were doubly digested with the use of PvuII and HindIII. Then the orientation of the inserted fragments was identified. It was found that eight of the clones had the inserts with the correct orientation. Of these eight clones, the plasmids from five clones were doubly digested with the use of XbaI and HindIII, and the DNA that contained the inserted fragments were removed, subcloned into the phages M13mp18 and mp19. The base sequences were analyzed by the dideoxy method. Three of the clones were found to contain the desired sequence. The recombinant plasmids obtained in this way were named pTF101.

(1-7) Purification of Plasmids

The pTF101 obtained as described above in section (1-6) was used to transform *Escherichia coli* cells (SB221/pTF 101) and such transformed cells were cultured in 5 ml of L-broth overnight with agitation at 37° C. The culture was transferred to 500 ml of the same culture broth and culture was continued until the absorbance at 660 nm reached 0.6, at which time 170 µg/ml chloramphenicol was added, and cultured was continued once more for 10–12 hours. The culture broth was centrifuged for 10 minutes at 5000 rpm, and the cell pellet was washed in STE buffer (10 mM Tris-HCl, pH 8, 100 mM NaCl, and 1 mM EDTA), and centrifuged again in the same way in order to obtain the cell pellet. The pellet was suspended in 10 ml of the solution A, and kept at room temperature for 5 minutes before 20 ml of the solution B was added with rapid stirring, and the suspension was left for 5 minutes at 0° C. To this suspension, 15 ml of 3M potassium acetate was added with rapid stirring, and the suspension was left at 0° C. for 10 minutes. The mixture was centrifuged for 60 minutes at 8000 rpm and the supernatant was obtained, to which 27 ml (0.6 volume) of isopropyl alcohol was added, and the mixture was left at room temperature for 15 minutes. This mixture was centrifuged and the precipitate was collected and washed in 80% ethanol. The ethanol and water in the resulting mixture was removed under reduced pressure and the residue was dried. This residue was dissolved in 4 ml of TE buffer and to this solution, 4.75 g of cesium chloride was added, followed by the addition of 5 mg/ml ethidium bromide in the volume of 420 µl; the mixture was left for 30 minutes 0° C. The mixture was then centrifuged for 10 minutes at 8000 rpm, and the supernatant was put into a Bechman Quick-seal tube and ultracentrifuged at 55000 rpm overnight. Then, under ultraviolet light, plasmid bands were removed by the use of a syringe. The resulting mixture was extracted seven times in equal volumes of isopropyl alcohol and the remaining ethidium bromide was removed, after which ethanol precipitation was done twice, and then the remaining mixture was washed in 80% ethanol, dried under reduced pressures, and dissolved in a small amount of TE buffer (yield, 760 µg).

EXAMPLE 2

Cloning of the cDNA fragment that codes for Ala$^{1235}$-Met$^{1517}$ (283 amino acid residues) of fibronectin (see FIG. 2):

First, 50 µg of the plasmid pLF5 was put into 200 µl of a reaction mixture containing 200 units of EcoRI methylase in a buffer for use with EcoRI methylase (100 mM Tris-HCl, pH 8.0, 2 mM DTT, 10 mM EDTA, and 80 µM S-adenosylmethionine), and the mixture was incubated for 60 minutes at 37° C. to bring about protection of the EcoRI sites. Then the reaction was stopped by being heated at 65° C. for 20 minutes, and 96 units of PvuII in buffer for use with PvuII was added; 300 µl of the reaction mixture was incubated for 60 minutes at 37° C. This mixture was separated by agarose electrophoresis, and the slice of gel containing 0.60 kb band was cut out. This slice was put into a dialysis tube that contained elution buffer (5 mM Tris-acetate buffer, pH 8.0, and 1 mM EDTA), and elution by electrophoresis occurred in the same buffer, by which means the DNA was eluted. The elution fluid was extracted twice with phenol, and a 1/10 volume of 3M sodium acetate was added, followed by the addition of two volumes of ethanol, and ethanol precipitation was conducted twice. Then the resulting mixture was washed in 80% ethanol, dried, and dissolved in a small amount of TE buffer (yield, 1.2 ug).

Also, 140 µg of the plasmid pTF101 obtained in Example 1 was put into 200 µl of a reaction solution containing 144 units of PvuII, and the mixture was incubated for 60 minutes at 37° C. Then 150 units of EcoRI was added, and the reaction solution brought to 240 µl, and incubated for 60 minutes at 37° C. The result was separated by polyacrylamide electrophoresis, and the bands at 0.25 kb were cut out. The DNA was extracted from these bands of gel as described above, and the DNA was collected by ethanol precipitation (yield, 0.4 µg). Then 1.25 µg of the 0.6-kb fragments obtained here and 0.4 ug of the 0.25-kb fragments were put into a ligation buffer which contains 2.8 units of T4 DNA ligase, 0.5 mM ATP, and 10 mM DTT in 50 µl, and the mixture was incubated for 30 minutes at 16° C. Then 92 pmol of phosphorylated linker (pCCGAATTGG) and 1.4 units of T4 DNA ligase were added to the reaction mixture, which was brought to 70 µl and incubated overnight at 10° C. The reaction was stopped by heating at 65° C. for 10 minutes, and the buffer was modified to be suitable for EcoRI; 30 units of EcoRI was added, and reaction was allowed to take place for 60 minutes at 37° C. Then the reaction mixture was separated by agarose electrophoresis, and the 0.86-kb bands were cut out. The DNA in the bands was obtained by the method described above (yield, about 25 ng). Then 20 ng of the 0.86-kb fragments were cleaved with EcoRI, and put into a ligation buffer which contains 0.1 µg of dephosphorylated vector pIN-III-OMPA-1, 2.8 units of T4DNA ligase, 0.5 mM ATP, and 10 mM DTT in a total volume of 20 µl; the mixture was incubated for 10 hours at 16° C. and half of the reaction was used to transform *Escherichia coli* SB 221 cells by the method described above. Of the transformants obtained, 48 of the clones were analysed for plasmids by the methods described above, and it was found that the plasmids included the desired fragments in six of the clones. These six plasmids were digested with BamHI, and the fragments which were produced were analysed. Five of the clones contained the desired fragments inserted in the correct orientation. Three of these five clones were studied for their base sequence. One of the clones was found to have the correct base sequence. This recombinant plasmid was named pTF301, and the cells of *Escherichia coli* SB221 that carry this plasmid were designated SB221/pTF301.

EXAMPLE 3

Cloning of the cDNA fragment which codes for Pro$^{1239}$-Met$^{1517}$ (279 amino acid residues) of fibronectin (see FIG. 3):

(3-1) Preparation of cDNA fragments

First, 100 µg of the plasmid pTF301 which codes for peptide 283AA with cell-spreading activity was mixed with a buffer for use with the restriction enzyme XbaI and with 120 units of XbaI in a total volume of 300 µl, and incubated at 37° C. for 2 hours. Then, the DNA was collected by ethanol precipitation. Half of the amount obtained was put into 375 µl of a reaction mixture of buffer for use with BAL 31 nuclease which contained 36 units of BAL 31 nuclease-S, and the mixture was incubated at 30° C.; at 2 minutes of incubation to 8 minutes, 28 µl of the reaction mixture was sampled every 30 seconds, and each sample was added to 20 µl of 0.5M EDTA to stop the reaction. The samples were pooled, and DNA was obtained by phenol treatment and then ethanol precipitation. The DNA obtained was put into 200 µl of a reaction mixture of 7 mM Tris-HCl, pH 7.5, which contained 0.1 mM EDTA, 10 mM NaCl, 7 mM MgCl$_2$, 0.1 mM dATP, dGTP, dCTP, and dTTP, and 2 units of Klenow fragment. The mixture was incubated for 20 minutes at 37° C. The reaction was stopped by treatment at 65° C. for 10 minutes, and the reaction mixture was adjusted to the composition of buffer for use with HindIII. Then, to 250 µl of this reaction mixture, 60 units for HindIII was added, and the mixture was incubated for 1 hour at 37° C. This mixture was separated by agarose gel electrophoresis, and the fragments that correspond to the size of 0.5–0.8 kb were cut out; 1 µg was obtained.

(3-2) Cloning into pUC119N

First, 0.65 µg of the DNA fragments obtained in section (3-1) above was put into 30 µl of a ligase buffer which contained 0.5 µg of phosphorylated NcoI linker (d[pAGCCATGGCT]), 2.8 units of T4 DNA ligase, 0.5 mM ATP, and 10 mM DTT; and the mixture was incubated overnight at 10° C. After the reaction was stopped by being heated at 65° C. for 10 minutes, 24 units of NcoI and 12 units of HindIII were added to this reaction mixture and the mixture was incubated in a total volume of 50 µl for 1 hour at 37° C. This was put on a 1-ml column of Sepharose CL-4B; the free linker was eluted with STE buffer.

Then 300 µl of DNA fraction was obtained and concentrated to 55 µl. Of this, 5.5 µl was added to 1 µl of a solution that contained 0.2 µg of the plasmid pUC119 that had been dephosphorylated by treatment with NcoI and HindIII. To this, 65 µl of solution A and 6.5 µl of solution B from a DNA ligation kit (Takara Shuzo Co., Ltd.) were added, and the mixture was incubated overnight at 16° C. Then 20 µl of the reaction mixture was used to transform cells of *Escherichia coli* HB 101.

In addition, pUC119N was obtained by creation of a NcoI site surrounding the translation initiation codon of the commercially available vector pUC119 (Takara Shuzo Co., Ltd.); the distance between the ribosome-binding site and initiation codon was also changed from 7 to 8 bases.

(3-3) Screening of the expression plasmids

The transformants obtained in section (3-2) above were transferred to a nitrocellulose filter (BA85; S & S) on L-agar medium containing 50 µg/ml ampicillin, and cultured overnight at 37° C. The colonies that grew were brought into chloroform vapor for 15 minutes, and the nitrocellulose filter was put into a solution of 50 mM Tris-HCl, pH 7.5, containing 150 mM NaCl, 5 mM MgCl$_2$, 3% bovine serum albumin, 1 µg/ml DNase, and 40 µg/ml lysozyme; the mixture was incubated overnight at room temperature. The filter was treated with an anti-FN monoclonal antibody, FN-10 (Tarara Shuzo Co., Ltd.) which specifically recognizes the cell-spreading domain of FN, and a second antibody labelled with peroxidase was applied, and the hydrogen peroxide gave rise to color in the presence of 4-chloro-1-naphthol, by which the transformants which had appeared were found. By this first screening, 52 clones were selected from 1300 clones, and each was cultured overnight with agitation at 37° C. on 5 ml of L-broth containing 50 µg/ml ampicillin. The whole-cell protein of the cells obtained was separated on SDS-polyacrylamide gel electrophoresis (SDS-PAGE), and immunoblotting was applied, in which the anti-FN monoclonal antibody FN-10 was allowed to react. It was found that polypeptides of the molecular masses of 22 kDa-32 kDa had been produced. For 11 clones, the base sequence of the 5'-end of the inserted fragments was identified; they were found to code amino acid sequences which were respectively 279, 258, 219, 213, 207, 206, 198, 195, 190, 186, and 178 long counting from Met$^{1517}$ as the C-terminus.

The amount of these peptides which were expressed were compared on SDS-PAGE; the peptide which was expressed in the greatest amount was a peptide with a sequence 279 amino acids long (accounting for about 20% of the total whole-cell protein); next were peptides with sequence 206 and 258 amino acids long.

The plasmid which expressed the peptide with the sequence 279 amino acids long was designated pTFD707. At the N-terminus of the peptide expressed by pTFD707, there was a sequence (GCT) attached that corresponded to alanine of vector origin. This sequence was removed by site-specific mutagenesis (a procedure used, for example, in Example 4 of U.S. Ser. No. 291,894). Also, in order to raise the level of expression, the HindIII-SalI fragment with a lpp terminator sequence was removed from the secretion-expression vector pIN-III-ompA-I, and joined with the HindIII-SalI site of pTFD707, by which means plasmids designated pTF7021 were obtained.

EXAMPLE 4

Construction of the plasmid which codes for Pro$^{1239}$-Asp$^{1512}$ (274 amino acid residues) of fibronectin: (see FIG. 4):

Introduction of mutation into pTFD707 was done by the method of Kunkel et al. (Proceedings of the National Academy of Sciences, U.S.A., 82, 488–492, 1985; Methods in Enzymology, 154, 367–382, 1987). For this purpose, the site-directed mutagenesis system, Mutan-K(Takara Shuzo) was used.

pTFD707 was introduced into *Escherichia coli* BW313, and the transformants were cultured with agitation at 37° C. on 100 ml of 2×YT medium (1.6% Bactotrypton, 1% yeast extract, and 0.5% NaCl) that contained 50 µg/ml ampicillin. When the absorbance at 660 nm was 0.3, 1 ml of M13K07 phage suspension containing 10$^{10}$ pfu was added to the culture, and cultivation was continued at 37° C. for 16 hours. The culture medium was centrifuged and the supernatant collected; to this supernatant, 25 ml of a mixture of 2.5M NaCl and 20% polyethlene glycol 6000 was added, and the resulting mixture was left for 10 minutes at room temperature. It was then centrifuged, and 5 ml of TE buffer was added to the precipitate. This mixture was treated with a mixture of phenol and chloroform, and then with chloroform alone, before ethanol precipitation was used to give single-stranded DNA. The 30 ng of single-stranded DNA obtained was dissolved in 1 µl of annealing buffer(20 mM Tris-HCl, pH 8.0, 10 mM MgCl$_2$, 50 mM NaCl, and 1 mM DTT), and added to 1 µl of a solution that contained 1 pmol of phosphorylated oligonucleotide d[pGGATGGTTAGTCAATTTC], and the mixture was treated by heat at 65° C. for 15 minutes and at 37° C. for 15 minutes. The resulting mixture was added to 25 µl of extension buffer(50 mM Tris-HCl, pH8.0, 60 mM ammonium acetate, 5 mM MgCl$_2$, 5 mM DTT, 1 mM NAD, 0.5 mM dATP, dGTP, dCTP and dTTP), with 60 units of DNA ligase from *E. coli* and 1 unit of T4 DNA polymerase, and the reaction mixture was left at 25° C. for 2 hours, before 3 μl of a 0.2M solution of EDTA, pH 8.0, was added, and the reaction mixture was heated at 65° C. for 5 minutes. Then, 3 μl of the reaction mixture was mixed with 30 μl of competent cells of *Escherichia coli* BMH71-18mutS, and the mixture was kept at 0° C. for 30 minutes, at 42° C. for 45 seconds, and at 0° C. for 2 minutes. Then 300 μl of L-broth was added, and the mixture was left for 1 hour at 37° C. Next, 10 μl of a suspension of M13K07 phages was added, and the mixture was left for 30 minutes at 37° C. Next, the cells were cultured for 16 hours at 37° C. with agitation in 1 ml of 2×YT medium that contained 150 μg/ml ampicillin and 70 μg/ml kanamycin. The culture was centrifuged and the supernatant collected. Then 20 μl of the supernatant was mixed with 80 μl of the culture medium of an overnight culture of *Escherichia coli* JM109. This was left for 10 minutes at 37° C., and one portion was used to inoculate L-agar that contained 50 μg/ml ampicillin; the agar was left at 37° C. overnight, and of the transformants that were obtained, the base sequences of six of the clones were identified. Of these six clones, five were found to have the desired mutation. The recombinant plasmid obtained was designated pTFD707-45.

Then, 2 μg of pTFD707-45 was digested with BamHI and HindIII, the resulting digest was separated on agarose gel electrophoresis, and the 0.5-kb fragment was collected. Separately, 2 μg of pTF7021 was digested with BamHI and ScaI, and the digest separated on agarose gel electrophoresis. The 2.1-kb fragment was obtained. Next, 2 μg of pTF7021 was digested with HindIII and ScaI, and the digest separated on agarose gel electrophoresis, and the 2.4-kb fragment collected. To 3 μl of a solution that contained 5 ng of the 0.5-kb fragment, 20 ng of the 2.1-kb fragment, and 20 ng of the 2.4-kb fragment, 12 μl of solution A and 3 μl of solution B from a DNA ligation kit (Takara Shuzo) were added, and incubation was done at 16° C. for 30 minutes. Then 10 μl of the reaction mixture was used to transform cells of *Escherichia coli* JM109. A plasmid was obtained that coded for the Pro$^{1239}$-Asp$^{1512}$ sequence 274 amino acids long of FN, and that also had the lpp terminator sequence. This recombinant plasmid was named pTF7221, and the cells of *Escherichia coli* JM109 that carried this plasmid were designated *Escherichia coli* JM109/pTF7221. The strain was deposited at the Fermentation Research Institute of the Agency of Industrial Science and Technology, Japan, under FERM BP-1915.

Cells of JM109/pTF7221 were cultured and it was checked whether they expressed a polypeptide with cell-spreading activity; it was found that this protein accounted for at least 30% of the whole-cell protein.

EXAMPLE 5

Purification of the Pro$^{1239}$-Asp$^{1512}$ polypeptide (274 amino acid residues) of fibronectin:

Plasmid pTF7221 obtained by the joining of an expression vector and the DNA that codes for the Pro$^{1239}$-Asp$^{1512}$ sequence of FN (a sequence of 274 amino acid residues) was introduced into *Escherichia coli* JM109, giving *Escherichia coli* JM109/pTF7221, and these cells were cultured overnight with shaking at 37° C. in 5 ml of L-broth containing 50 μg/ml ampicillin in a test tube. This was used to inoculate a 2-1 Erlenmeyer flask containing 500 ml of the same medium, and culture was continued at the agitation rate of 180 r.p.m. When absorbance at 660 nm had reached 0.3, 2 mM IPTG (isopropyl-β-thiogalactoside) was added, and the cells were harvested 20 hours later. One portion of the cells obtained was used in immunoblotting. The whole-cell protein was isolated by SDS-PAGE, and the electrophoretic pattern was transferred to a nitrocellulose membrane. Then a monoclonal antibody (FN-10, Takara Shuzo Co., Ltd.) that specifically recognizes the cell-spreading domain of FN was applied, after which a second antibody labelled with peroxidase was applied. The activity of the peroxidase bound to the second antibody gave rise to color in the presence of 4-chloronaphtol and hydrogen peroxide, and it was found that the desired band in the region of 34 kDa lower molecular band than that of 279 amino acid residues was present. Next, the whole-cell pellet was suspended in a solution of 10 mM Tris-HCl, pH 7.5, containing 5 mM EDTA and 5 mM mercaptoethanol, and ultrasonification was conducted. This suspension was centrifuged and the supernatant was obtained and dialyzed against 20 mM Tris-HCl (pH 7.5). The inner dialysis liquid was put on a Sepharose 4B column (8 ml) bound with the monoclonal antibody FN-10. The column was washed with washing buffer A (20 mM Tris-HCl, pH 8.0, and 0.15M KCl), and then with washing buffer B (20 mM Tris-HCl, pH 6.4, and 0.15M KCl). Finally, the eluting buffer (50 mM glycine-HCl, pH 2.3, and 0.2M KCl) was used, and fractions were obtained. The desired fractions were obtained by immunoblotting, desalted, and lyophilized, and about 5 mg of almost pure peptide was obtained by electrophoresis. Next, said peptide was treated with aminopeptidase P (*Enzyme Handbook*, p. 534 (1983), Asakura Publishers), and the N-terminal methionine was removed, after which the peptide was purified again by the same method as described above. The 10 or so amino acids residues in the amino acids residues in the amino acid sequence starting from the N-terminus were studied, and it was found that the sequence was Pro-Thr-Asp-Leu-Arg-Phe-Thr-Asn-Ile-Gly, which agreed with the N-terminal sequence of the desired peptide.

EXAMPLE 6

Measurement of Cell-Spreading Activity

The cell-spreading activity of the polypeptide of 274 amino acid residues obtained in Example 5 and of FN and the peptides with 108 and 279 amino acids was measured by the method of Ruoslahti et al. (*Methods in Enzymology*, 82, 803–831, 1981). The samples was diluted stepwise in physiological saline and distilled water, and 50 μl of the resultant solution was injected into the wells of a 96-well microtitre plate, which was then incubated overnight at 4° C. in order to allow the sample to adhere to the wells. Then, phosphate-buffered saline (PBS) was used to wash the plate twice, 100 μl of 3% BSA was added to each well, and the plate was incubated for one hour at 37° C. The plate was washed twice with PBS, and then normal rat kidney (NRK-49F) cells suspended to the concentration of 10$^6$ cells/ml in Eagle's Minimum Essential Medium (MEM) were added in the amount of 100 μl/well, and the plate was incubated for 2–3 hours at 37° C. The NRK-49F cells that were used were obtained as a lyophilized strain for storage, and first preincubated and then treated with trypsin before use. The spreading of the cells was observed under a microscope, and the minimum dose needed to have cell-spreading activity was calculated. These results are shown in Table 1.

TABLE 1

| Polypeptide (length of amino acid sequence) | Minimum dose for cell spreading μg/well (p mole/well) |
|---|---|
| Ile$^{1410}$-Met$^{1517}$ (108) | >50 (>4400) |
| Pro$^{1239}$-Asp$^{1512}$ (274) | 0.03 (1.0) |
| Pro$^{1239}$-Met$^{1517}$ (279) | 0.03 (1.0) |
| Fn (2324) | 0.18 (0.8) |

As explained above in detail, this invention provides a peptide which has cell-spreading activity essentially the same as that of FN, and also provides a method for its preparation by the use of genetic engineering. The polypeptides mentioned above can be used as a pharmaneutical preparation for such uses as for the healing of wounds, in collyria, for the prevention of metastases from cancer, for the implantation of artificial organs into the body, and the like. It can also be used in cosmetics, toothpaste, and the like.

What we claim is:

1. A polypeptide with cell-spreading activity which consists of the following amino acid sequence beginning with the amino terminus:

Pro Thr Asp Leu Arg Phe Thr Asn Ile Gly Pro Asp Thr Met

-continued

Arg Val Thr Trp Ala Pro Pro Pro Ser Ile Asp Leu Thr Asn

Phe Leu Val Arg Tyr Ser Pro Val Lys Asn Glu Glu Asp Val

Ala Glu Leu Ser Ile Ser Pro Ser Asp Asn Ala Val Val Leu

Thr Asn Leu Leu Pro Gly Thr Glu Tyr Val Val Ser Val Ser

Ser Val Tyr Glu Gln His Glu Ser Thr Pro Leu Arg Gly Arg

Gln Lys Thr Gly Leu Asp Ser Pro Thr Gly Ile Asp Phe Ser

Asp Ile Thr Ala Asn Ser Phe Thr Val His Trp Ile Ala Pro

Arg Ala Thr Ile Thr Gly Tyr Arg Ile Arg His His Pro Glu

His Phe Ser Gly Arg Pro Arg Glu Asp Arg Val Pro His Ser

Arg Asn Ser Ile Thr Leu Thr Asn Leu Thr Pro Gly Thr Glu

Tyr Val Val Ser Ile Val Ala Leu Asn Gly Arg Glu Glu Ser

Pro Leu Leu Ile Gly Gln Gln Ser Thr Val Ser Asp Val Pro

Arg Asp Leu Glu Val Val Ala Ala Thr Pro Thr Ser Leu Leu

Ile Ser Trp Asp Ala Pro Ala Val Thr Val Arg Tyr Tyr Arg

Ile Thr Tyr Gly Glu Thr Gly Gly Asn Ser Pro Val Gln Glu

Phe Thr Val Pro Gly Ser Lys Ser Thr Ala Thr Ile Ser Gly

Leu Lys Pro Gly Val Asp Tyr Thr Ile Thr Val Tyr Ala Val

Thr Gly Arg Gly Asp Ser Pro Ala Ser Ser Lys Pro Ile Ser

Ile Asn Tyr Arg Thr Glu Ile Asp.

* * * * *